United States Patent [19]

Robbins

[11] Patent Number: 4,466,433
[45] Date of Patent: Aug. 21, 1984

[54] OVERPRESSURE RELIEF SYSTEM

[75] Inventor: David L. Robbins, St. Paul, Minn.

[73] Assignee: Minnesota Mining and Manufacturing Company, Saint Paul, Minn.

[21] Appl. No.: 327,552

[22] Filed: Dec. 4, 1981

[51] Int. Cl.³ .......................................... A61M 16/00
[52] U.S. Cl. ............................ 128/202.22; 128/205.24; 128/204.25; 128/205.23
[58] Field of Search ....................... 128/202.22, 204.18, 128/204.19, 204.21, 204.23, 204.24, 205.23, 205.24, 204.25

[56] References Cited

U.S. PATENT DOCUMENTS

| 3,039,481 | 6/1962 | Schreiber et al. | 128/204.19 |
| 3,863,630 | 2/1975 | Cavallo | 128/204.23 |
| 3,985,131 | 10/1976 | Buck et al. | 128/204.21 |
| 4,039,139 | 8/1977 | Bird | 251/65 |
| 4,057,059 | 11/1977 | Reid, Jr. et al. | 128/204.24 |
| 4,148,313 | 4/1979 | Bird et al. | 128/204.19 |
| 4,164,219 | 8/1979 | Bird | 128/204.19 |
| 4,232,666 | 11/1980 | Savelli et al. | 128/203.25 |
| 4,340,044 | 7/1982 | Levy et al. | 128/204.21 |

Primary Examiner—Henry J. Recla
Attorney, Agent, or Firm—Donald M. Sell; James A. Smith; William L. Huebsch

[57] ABSTRACT

An infant ventilator is described of the type that switches between an inspiration phase during which gas under pressure is applied through a mouthpiece to cause involuntary inspiration of the infant to which the mouthpiece is coupled, and an expiration phase during which the infant is allowed to exhale or voluntarily inhale through the mouthpiece while gas flows past the mouthpiece. An overpressure relief system is included to monitor the pressure in the patient circuit and react to pressures above an operator-selected level by halting inflow of gas into the patient circuit, exhausting patient pressure to the atomsphere, and producing an alarm.

5 Claims, 4 Drawing Figures

OVERPRESSURE RELIEF SYSTEM

TECHNICAL FIELD

This invention relates to infant ventilators of the type that switch between an inspiration phase during which gas under pressure is applied through a gas delivery system to a mouthpiece to cause involuntary inspiration of an infant to which the mouthpiece is coupled, and an expiration phase during which the infant is allowed to exhale or voluntarily inhale through the mouthpiece while gas flows past the mouthpiece and through an outlet to the atmosphere; and in one important aspect to the means in such a ventilator for dealing with excessive pressure in the gas delivery system caused by occlusion of the system between the mouthpiece and the outlet or elsewhere.

BACKGROUND ART

Gas flow past the mouthpiece during the expiration phase in an infant ventilator of the type described above is important to both sweep exhaled gases from the mouthpiece to ensure that the infant will not inhale his own exhaled gases, since the mouthpiece holds a large volume of gas compared to the volume of an infant's breath; and to provide gas which the infant may voluntarily inhale during the expiratory phase, since it is difficult to design a ventilator that can be switched to an inspiration phase by an infant's weak attempts to inhale.

Typically in the type of infant ventilator described above, the gas delivery system includes a flexible hose through which the gas flows past the mouthpiece and to an outlet end of the hose spaced from the mouthpiece. An outlet valve is positioned at the outlet end of the hose, which outlet valve is movable via control means for the ventilator between (1) a closed position blocking the outlet end of the hose so that gas pressure at the mouthpiece will increase sufficiently to cause involuntary inspiration of an infant to which the mouthpiece is coupled (the inspiration phase of the ventilator), and (2) an open position so that gas will flow past the mouthpiece and through the outlet end of the hose to the atmosphere (the expiration phase of the ventilator).

Problems arise in such prior art infant ventilators when the hose between the mouthpiece and the outlet is occluded, as can happen when the hose is inadvertently crimped. Known prior art infant ventilators include no means for shutting off the inflow of gas through the gas delivery system when such an occlusion occurs so that the gas pressure at the mouthpiece can quickly reach dangerous levels. Those known prior art ventilators deal with this hazard by providing a spring-loaded relief valve positioned in the gas delivery system upstream of the mouthpiece, which relief valve will vent incoming gas flow to the atmosphere when pressure in the delivery system exceeds a predetermined set level (generally the maximum pressure the gas deliver system will normally apply to an infant). Should such an occlusion persist with those prior art infant ventilators, an infant being ventilated will be subjected to sustained high pressure, which situation is potentially very hazardous.

DISCLOSURE OF INVENTION

The present invention provides an overpressure relief system for an infant ventilator generally of the type described above, which relief system senses pressure within a patient gas delivery system between its inlet end and the mouthpiece and reacts to pressures above a preset maximum by halting inflow of gas into the gas delivery system and also by exhausting to the atmosphere the pressure in the portion of the gas delivery system including the mouthpiece.

According to the present invention there is provided an infant ventilator comprising (1) a gas delivery system including an inlet end adapted to be coupled to a source of gas under pressure, a mouthpiece between the inlet end and an outlet end, which mouthpiece is adapted to be coupled to the breathing passageways of an infant, an outlet valve at the outlet end movable between a closed position so that the gas pressure at the mouthpiece will increase sufficiently to cause involuntary inspiration of the infant to which the mouthpiece is coupled, and an open position at which gas can flow past the mouthpiece to allow exhalation of the infant, remove any exhaled gases from the mouthpiece, and afford voluntary inhalation of the infant; (2) means for sensing pressures above a predetermined maximum in the gas delivery system between the inlet end and the mouthpiece; and (3) means activated by the sensing means when it senses a pressure within the gas delivery system above the predetermined maximum for stopping the inflow of gas into the patient gas delivery system and also for exhausting to the atmosphere a portion of the patient gas delivery system including the mouthpiece.

In a preferred embodiment of the present invention the means for sensing comprises an activator including a permanent magnet fixed within a housing, and a shaft assembly within the housing and extending on both sides of the magnet, which shaft assembly is mounted for axial sliding movement between first and second position. The shaft assembly includes inner and outer magnetically attractable plates or members fixed to a shaft on opposite sides of the magnet. The outer member is closely adjacent to the magnet and the inner member is spaced from the magnet when the shaft assembly is in its first position; and the inner member is closely adjacent to the magnet and the outer member is spaced from the magnet when the shaft assembly is in its second position. In either position the magnetic attraction between the magnet and the adjacent member will bias the shaft assembly into the position in which it is positioned in opposition to the weaker magnetic attraction between the magnet and the spaced member, so that the actuator is bistable. A diaphragm is coupled to the shaft adjacent the inner member, and with the housing defines a chamber coupled to the gas delivery system so that when the shaft assembly is in its first position, pressure above the predetermined maximum in the chamber will move the diaphragm and thereby the shaft assembly toward its second position until the magnetic attraction between the magnet and the inner member exceeds the magnetic attraction between the magnet and the outer member and causes the shaft assembly to suddenly shift to its second position.

As the shaft assembly is thus suddenly moved to its second position, it can actuate a switch which via an electrical circuit and a series of electrically and pneumatically operated valves can stop the flow of gas through the gas delivery system, and exhaust the portion of the gas delivery system including the mouthpiece; and can additionally activate an alarm which may be audible, visible, or both.

BRIEF DESCRIPTION OF THE DRAWING

The present invention will be further described with reference to the accompanying drawing wherein like reference numerals refer to like parts in the several views and wherein.

DESCRIPTION OF PREFERRED EMBODIMENT

Figure 1:
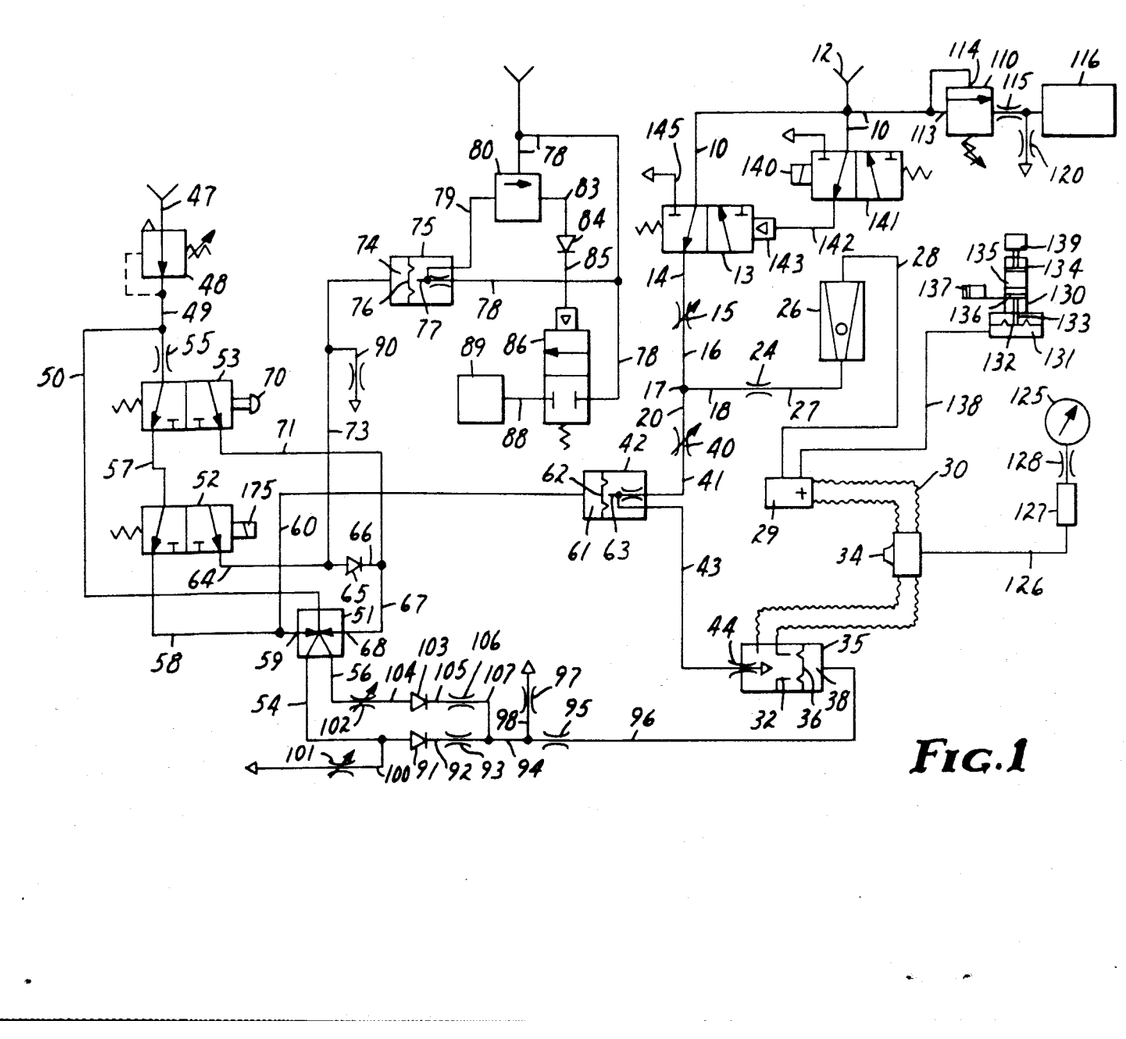
FIG. 1 is a schematic view of a gas delivery system for an infant ventilator including an overpressure relief system according to the present invention.

Referring now to FIG. 1 there is shown a schematic diagram of a gas delivery system for an infant ventilator including an overpressure relief system according to the present invention.

Generally, the gas delivery system includes a supply portion comprising a gas supply network 10 having an inlet end 12 defining a first end for the supply portion adapted to be coupled to a source of gas under pressure (e.g. a mixture of air and oxygen) and coupled at its opposite end to an inlet port of a gas-operated spring return spool valve 13 that provides a portion of an overpressure safety system to be explained later, a line 14 connecting a first outlet port of the spool valve 13 to a manually-adjustable flow control needle valve 15, and a line 16 connecting the valve 15 to a junction 17 with lines 18 and 20, which junction 17 defines a second end for the supply portion of the gas delivery system. The gas delivery system also includes a patient delivery portion including the line 18 and having an inlet end defined by the end of the line 18 coupled to the junction 17. The end of the line 18 opposite the junction 17 is coupled to a restriction 24 that limits gas flow through the patient delivery portion to a rate in the range of from about 0 to 25 liters per minute; which rate may be set by manual adjustment of the flow control valve 15 and will be indicated on a Thorp tube 26 coupled to the restriction 24 by a line 27. A line 28 connects the outlet of the Thorp tube 26 to the inlet end 29 of a flexible hose 30. The hose 30 has an outlet end 32 opposite its inlet end 29, a mouthpiece 34 between its ends 29 and 32 adapted to be coupled to the breathing passageways of an infant. An outlet valve 35 is positioned at the outlet end 32 of the hose 30 and includes a diaphragm 36 adapted to be moved between (1) a closed position (not shown) to which it can be urged by air pressure in a chamber 38 coupled to a switching system later to be explained, at which closed position the diaphragm 36 closes the outlet end 32 of the hose 30 to cause gas pressure at the mouthpiece 34 to increase sufficiently to cause involuntary inspiration of an infant to which the mouthpiece 34 is coupled (the inspiration phase of the ventilator); and (2) a normally open position (illustrated in FIG. 1) at which the diaphragm 36 is spaced from the outlet end 32 of the hose 30 and gas can flow past the mouthpiece 34 and out the outlet end 32 of the hose 30 to the atmosphere (the expiration phase of the ventilator). A mouthpiece pressure-regulating portion of the gas supply system is provided by the line 20 which has an end coupled at the junction 17 that defines a first end for the mouthpiece pressure-regulating portion. The line 20 is coupled to a restriction or needle valve 40 intended to be adjusted once when the gas delivery system is assembled and to then remain fixed except for possible recalibration by a serviceman. A line 41 couples the restriction 40 to a diaphragm amplifier 42 that provides a part of the switching system later to be explained, which in turn is coupled by a line 43 to a venturi 44 in the hose 30 at its outlet end 32. The venturi 44 includes a small jet (i.e., preferably about 0.04 centimeter or 0.016 inch in diameter) directed so that it will discharge through the outlet end 32 of the hose 30 and so that the throat of the venturi 44 will reduce the gas pressure at the outlet end 32 of the hose, and thus reduce the gas pressure at the mouthpiece 34 to essentially the same predetermined pressure during the expiration phase of the ventilator, which reduced pressure at the mouthpiece 34 will be about atmospheric or slightly above atmospheric pressure for any rate of gas flow set by the valve 15.

The portion of the gas delivery system that switches the outlet valve 35 between its open and closed position by releasing or applying air pressure from the chamber 38, and thus respectively causes the expiration and inspiration phases of the ventilator, is supplied by oxygen from an external source through a line 47. The line 47 is coupled to a pressure regulator 48 from which oxygen at a reduced pressure (e.g., 8 psi) is supplied by lines 49 and 50 to a digital amplifier 51 that may be switched via an electronically-operated spring return spool valve 52 operated by an electronic control circuit for the ventilator (FIGS. 2a and 2b) or by a manually-operable spring return spool valve 53 into either a line 54 to cause the chamber 38 of the outlet valve 35 to be pressurized and close the outlet end 32 of the hose 30, or into a line 56 to allow the pressure in the chamber 38 to escape and the outlet valve 35 to open via circuitry that will later be explained.

Oxygen is supplied to the inlet port of the manually-operable spool valve 53 past a restriction 55 in the line 49 that reduces the oxygen pressure (e.g., to about 2 to 3 psi), from which valve 53 oxygen is supplied to the inlet port of the electrically-operated spool valve 52 by a line 57 when the manually-operated spool valve 53 is in its normal position (illustrated in FIG. 1).

When the electrically-operated spool valve 52 is also in its normal position (as illustrated in FIG. 1), oxygen will pass through it and a line 58 coupled between its first outlet port and a first pilot port 59 of the digital amplifier 51 which causes the oxygen passing through the line 50 to pass into the line 56 which will allow pressure capable of closing the diaphragm 36 in the chamber 38 to escape so that the outlet valve 35 will be open and gas will flow past the mouthpiece 34 and out the outlet opening 32. Also, oxygen from the line 58 will pass via a line 60 to a chamber 61 in the diaphragm amplifier 42 so that a diaphragm 62 therein will close the open end of a tube 63 and cause gas from the line 41 to pass into the line 43 to the venturi 44 rather than escape through the open end of the tube 63 and a vent in the diaphragm amplifier 42 as happens when its chamber 61 is not pressurized during the inspiration phase of the ventilator. Thus while the gas flows out of the outlet end 32 of the hose 30 during the expiration phase of the ventilator, the venturi 44 is activated to reduce the gas pressure in the hose 30 at the mouthpiece 34.

Figure 2A:
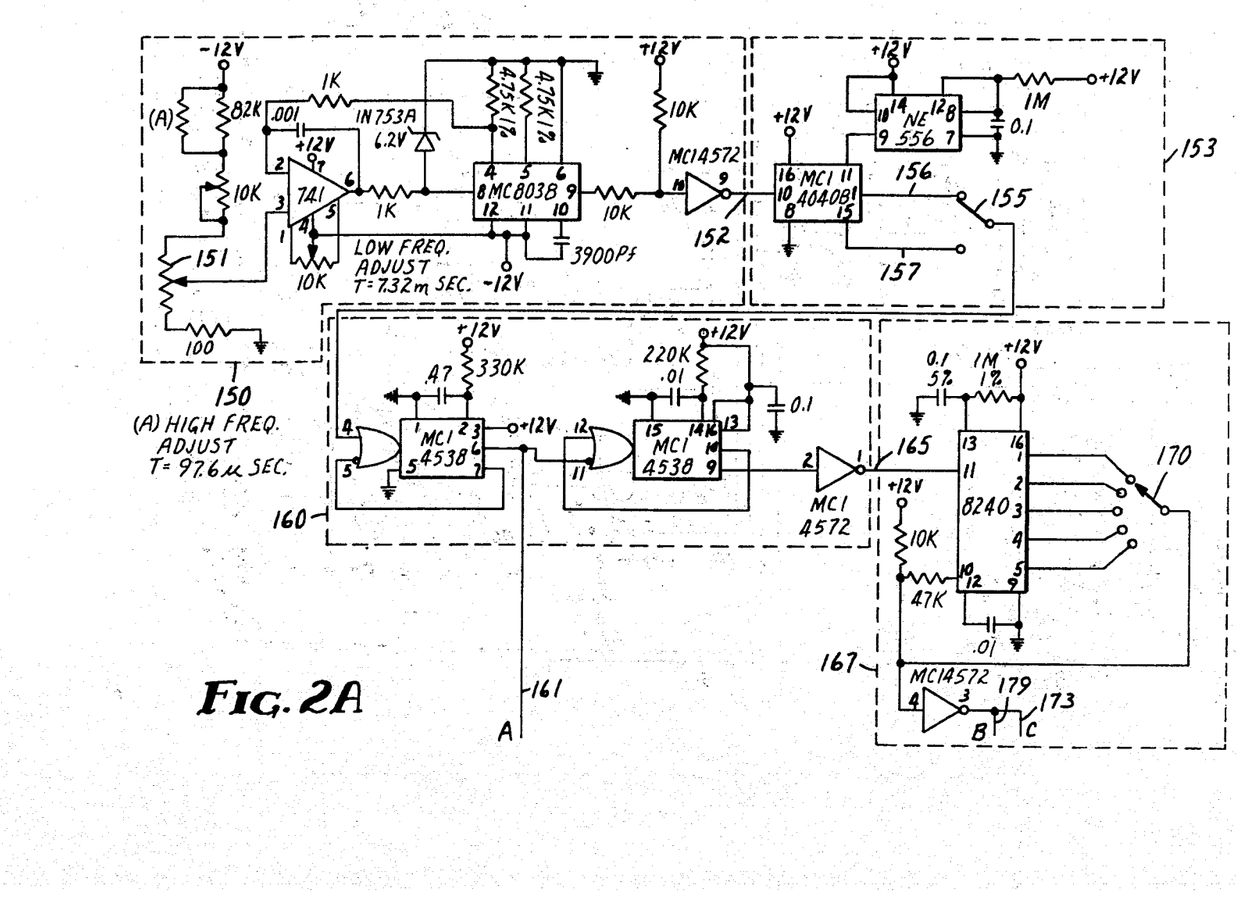
FIGS. 2A and 2B are schematic views of an electronic control circuit for controlling the gas delivery system of FIG. 1.
Figure 2B:
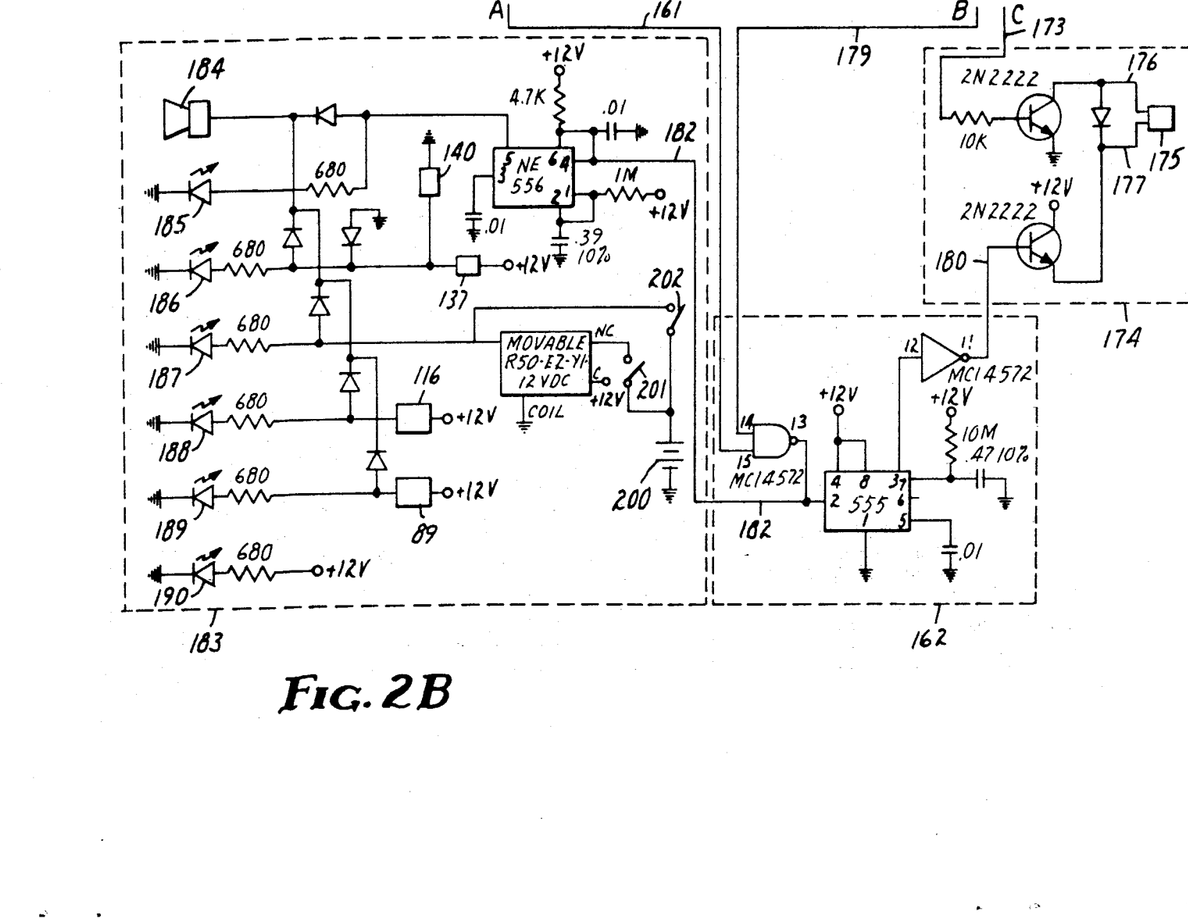

When the electronically-activated spool valve 52 is activated via the electronic circuit shown in FIGS. 2A and 2B, oxygen from the line 57 will pass out its second outlet port through a line 64, a one-way valve 65, and lines 66 and 67 to a second pilot port 68 of the digital amplifier 51 so that oxygen from the line 50 will pass into the line 54, the chamber 38 is pressurized, the outlet valve 35 is closed, and gas in the hose 30 is pressurized at the mouthpiece 34.

Alternatively, the manually-actuatable spool valve 53 can be activated by manual pressing of a knob 70 on the valve 53. When this is done, the oxygen supply to the electronically-actuated spool valve 52 will be blocked, and oxygen entering the inlet port of the manually-activatable spool valve 53 will pass out a second outlet port, through a line 71 and the line 67 to the second pilot port 68 of the digital amplifier 51 so that gas in the hose 30 will be pressurized as previously described. Thus the ventilator can be manually switched to its inspiration phase via the manually-activatable spool valve 53 at any time this is desired.

Circuitry is also provided for ensuring that the ventilator is not held in its inspiration phase for more than a predetermined length of time by activation of the electronically-activated spool valve 52 due to failure of the electronic control circuit or otherwise. A line 73 is coupled to the line 64 and receives oxygen pressure from the line 64 to pressurize a chamber 74 in diaphragm amplifier 75 when the spool valve 52 is activated. Pressure in the chamber 74 moves a diaphragm 76 in the diaphragm amplifier 75 into engagement with the open end of a tube 77 so that air from an air supply network 78 will pass through a line 79 into a time delay device 80. If the chamber 74 thus remains pressurized for longer than the predetermined time period (e.g., 3.5 seconds), the time delay device will connect air from the air supply network 78 to a line 83, cause it to pass through a one-way valve 84 and line 85 into the pilot port of an air-operated spring return poppet valve 86 so that the poppet in the valve 86 shifts to couple air from the air supply network 78 through a line 88 to a normally open switch 89 that will activate an alarm in the form of a horn 184 and a light emitting diode 189 (FIG. 2B). The one-way valve 84 will retain air pressure at the pilot port of the air-operated spool valve 86, so that the alarm cannot be deactivated except by a serviceman when the defect is corrected. If the electrically-activated spool valve 52 does not maintain the ventilator in the inhalation phase for the predetermined time period (as will normally be the case), after the electronically-operated spool valve 52 is deactivated air pressure in the chamber 74 will bleed off through the line 73 and a restricted open line 90.

The circuitry that couples the outlet line 54 from the digital amplifier 51 to the outlet valve 35 and supplies oxygen pressure to the chamber 38 to close the outlet valve 35 and cause the inspiration phase for the ventilator comprises a one-way valve 91, line 92, restriction 93, line 94, restriction 95 and line 96. The restrictions 93 and 95, a restriction 106 coupled to the line 94 by a line 107 and a restriction 97 open to the atmosphere and coupled to the line 94 by a line 98 have been selected to produce an inspiration pressure buildup and decay pattern designated a "modified shark-fin" in the industry, which pattern is believed to provide benefits to the infant being ventilated. A line 100 coupled between the line 54 and a manually-variable restriction or needle valve 101 having an outlet open to the atmosphere provides means to limit the amount of pressure that will be developed in the hose 30 to thereby limit the maximum gas pressure at the mouthpiece 34. As the valve 101 is opened it will allow more of the oxygen from the digital amplifier 51 to escape that would otherwise pressurize the chamber 38 in the outlet valve 35, so that pressure within the hose 30 can cause gas to escape to the atmosphere past the diaphragm 36 and thereby limit the gas pressure in the hose 30.

The circuitry that couples the outlet line 56 from the digital amplifier 51 to the outlet valve 35 and allows air pressure in the chamber 38 to escape so that the outlet valve 35 may open and cause the expiration phase for the ventilator comprises a manually-adjustable needle valve 102 coupled to a one-way valve 103 by a line 104, a line 105, the restriction 106, the line 107, the line 94, the restriction 95 and the line 96. The needle valve 102 is manually-adjustable so that it can either restrict flow of oxygen through the line 54 to an amount less than the amount that can escape to the atmosphere via the restriction 97 so that the outlet valve 35 will be fully open during the expiration phase, or it can pass a sufficient amount of oxygen so that the chamber 38 will be partially pressurized and the diaphragm 36 partially closed. Such partial closing of the diaphragm 36 will partially defeat the effect of the venturi 44 and cause a slight increase in the hose pressure at the mouthpiece 34 (PEEP), which may be desirable for some infants being ventilated.

The ventilator includes an alarm system that indicates if the pressure in the gas supply network 10 falls below a predetermined level. A spring biased normally open poppet valve 110 has both its inlet port and its pilot port coupled to the gas supply network 10 via lines 113 and 114 respectively so that gas pressure above a predetermined minimum holds the valve 110 closed. If gas pressure should fall below a predetermined level (e.g., 38 psi) a spring in the poppet valve 110 will overcome the gas pressure at its pilot port, cause the poppet valve 110 to open and gas to flow through the restricted line 115 to close a normally open gas-operated electrical switch 116 which will activate an alarm in the form of the horn 184 and a light-emitting diode 188 via the electronic circuit (FIGS. 2A and 2B). Gas will then also flow to the atmosphere through a restricted line 120 which serves to release gas pressure at the switch 116 and allow it to again open when the poppet valve 110 again closes upon gas pressure in the network 10 being restored to above the predetermined level.

A manometer 125 (e.g., reading from −10 to +80 cm $H_2O$) is provided for reading the pressure at the mouthpiece 34. The mouthpiece 34 is coupled to the manometer 125 via a flexible line 126, a quick disconnect coupling 127 that facilitates removal of the tube 126 with the hose 30, and a line 128 that is restricted to damp the reaction of the manometer 125 during pressure changes at the mouthpiece 34.

Figure 3:
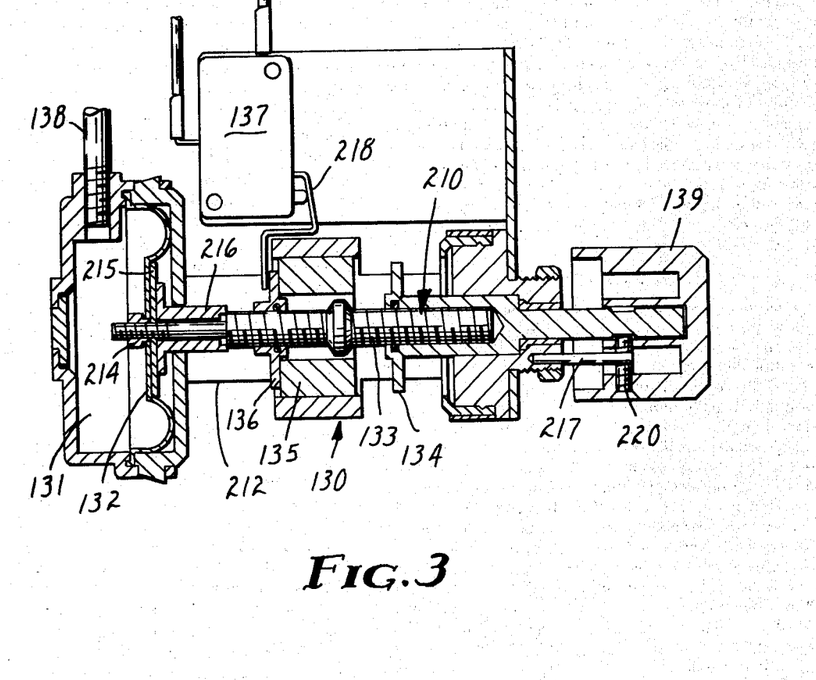
FIG. 3 is a cross sectional view of an activator included in the overpressure relief system.

The novel overpressure relief system according to the present invention that is provided in the ventilator will (1) stop the flow of gas through the gas delivery system, (2) exhaust a portion of the gas delivery system including the mouthpiece 34 to the atmosphere, and (3) can produce an alarm when a pressure above a predetermined maximum pressure (e.g. in the range of 30 to 80 cm $H_2O$) occurs in the delivery system between the inlet end 29 and the mouthpiece 34. The relief system includes an actuator 130 (best seen in FIG. 3) having a chamber 131 that will be pressurized by gas pressure at the inlet end of the hose 30 via a line 138. As pressure in the chamber 131 increases, diaphragm 132 which helps to define the chamber 131 will deflect and move an axially-slidable shaft assembly 210 within a housing 212 of the actuator 130 so that an outer magnetically attractable member or steel plate 134 mounted via threads on a shaft 133 (which shaft 133 is fixed at one end via a nut 214, plate 215, and collar 216 to the diaphragm) moves away from the force field of a permanent magnet 135 fixed within the housing 212 of the actuator 130. The force field of the magnet 135 can hold the outer plate 134 adjacent the magnet 135 over a range of movement of the shaft assembly 210 in generally a first normal position for the shaft assembly 210 (FIG. 1). Such movement of the outer plate 134 simultaneously moves a second inner magnetically attractable member or steel plate 136 threadably mounted on the shaft 133 (and spaced from the magnet 135 in the first portion of the shaft assembly 210) into the force field of the magnet 135 on the side of the magnet 135 opposite the outer plate 134. When the shaft assembly 210 is moved sufficiently by pressure in the chamber 131 so that the attraction between the inner plate 136 and magnet 135 overcomes the attraction between the outer plate 134 and magnet 135, the shaft assembly 210 will move suddenly to a second alarm position (FIG. 3) with the inner plate 136 closely adjacent to the magnet 135.

The space relationship between the magnet 135 and the outer plate 134 in the first position of the shaft assembly 210, and thus the pressure at which the shaft assembly moves to its alarm position, is adjustable via threaded engagement between the shaft 133 and an assembly including the outer plate 134 and a knob 139 fixed to the outer plate 134 via a set screw 220. That spacing can be changed to select a predetermined pressure (by rotating the knob 139 to move the outer plate 134 toward the magnet 135 to select a higher maximum pressure, or rotating the knob 139 to move the outer plate 134 away from the magnet 135 to select a lower maximum pressure; which rotations are limited by engagement of a pin 217 fixed to the housing 212 with the sides of the set screw 220 that fixes the knob 139 to the outer plate 134).

During movement of the shaft assembly 210 to its alarm position, the inner plate 136 will allow an operating lever 218 on a normally closed switch 137 to move to a normal position to which it is biased so that the switch 137 connects a voltage coupled to the switch 137 to a solenoid 140 of an electrically-operated spring return spool valve 141 via an electric line (FIG. 2B) and activates an alarm in the form of the horn 184 and a light-emitting diode 186. Such activation of the valve 141 will cause gas from the supply network 10 normally blocked by the valve 141 to flow through the valve 141 and a line 142 to pressurize the pilot port 143 of the air-operated spring return spool valve 13. Such pressure will actuate the spool valve 13, block the connection in the gas delivery system between the gas supply network 10 and the line 14 and allow pressure in the hose 30 to escape via the lines 28, 27 and 16 through an outlet port 145 of the valve 13 so that the high pressure in the hose 30 will no longer be present at the mouthpiece 34. After the problem causing the overpressure in the hose 30 has been corrected, the overpressure safety system can be re-set to its original condition by pressing the knob 139 toward the body of the activator 130 to return the axially-slidable shaft assembly 210 to its normal first position.

Referring now to FIGS. 2A and 2B there is illustrated the electronic control circuit for the infant ventilator that activates and deactivates the spool valve 52 to respectively cause the inspiration and expiration phases for the ventilator, and which provides several alarms and/or signal lights in response to several functions or malfunctions of the ventilator.

The circuit includes a square wave-generating portion enclosed by a dotted line 150 that is manually adjustable via a rotary potentiometer 151 calibrated in inspiration frequencies of from 0 to 75 inspirations per minute. The portion 150 generates a square wave having a frequency that is a high multiple of the frequency set at the potentiometer 151, which frequency is transmitted via a line 152 to a frequency divider portion 153 of the control circuit which produces a square wave on a line 154 that has either the same frequency as the frequency set on the rotary potentiometer 151 if a rocker switch 155 is set at a 1X position to connect a line 156 with the line 154; or that has a frequency that is two times the frequency set on the rotary potentiometer 151 if the rocker switch 155 is set at a 2X position to connect a line 157 with the line 154.

The line 154 transmits the square wave to a pulse width shaping portion of the circuit enclosed by a dotted line 160, which portion 160 produces a series of pulses at the same frequency as the square wave on the line 154, each of which pulses is 0.2 seconds in duration. This series of pulses is transmittted via a line 161 to a portion of the circuit enclosed by a dotted line 162, the function of which will later be explained; and just at the end of each pulse on the line 161, the pulse width shaping portion 160 transmits a much shorter pulse along a line 165 to a portion of the circuit enclosed by a dotted line 167 which determines the time duration for each inspiration phase of the ventilator.

The portion 167 that determines the time duration for each inspiration phase of the ventilator includes a rotary binary coding switch 170 calibrated for time durations of between 1 to 30 tenths of a second, which coding switch 170 may be manually set for any one of the calibrated time durations and will in response code the portion 167 of the circuitry to produce a series of signals of the selected time duration at the frequency of the pulses on the line 165. The portion 167 will then transmit that series of signals along a line 173 to a portion 174 of the circuitry that can activate a solenoid 175 on the spool valve 52 via lines 176 and 177 to cause the inspiration phases in response to the signals.

The signal along the line 173 is also transmitted via a line 179 coupled to the line 173 to the portion of the circuitry enclosed by the dotted line 162 that ensures that the frequency selected via the potentiometer 151 and rocker switch 155 and the time durations for each inspiration phase selected on the binary coding switch 170 will permit an expiration phase for the ventilator of at least 0.2 seconds, thereby ensuring that an infant to which the mouthpiece 34 is coupled has a safe period of time in which to exhale. If an expiration phase of at least 0.2 seconds is provided by the circuit, portion 180 will remain quiescent; but if it is not, the portion 162 will signal the portion 174 on a line 180 to prevent activation of the solenoid 175 for a period of 5 seconds, and via a line 182 will signal an alarm portion of the circuitry enclosed by the dotted line 183 to activate the horn 184 and light a light-emitting diode 185 to alert an operator of the problem. After 5 seconds the circuit portion 162 will allow the portion 174 to activate the solenoid 175 to cause a single inspiration phase, but if the problem has not been corrected, will then again stop activation of the solenoid 175 via the portion 174 for another 5-second period, after which this sequence is repeated until the problem is corrected.

In addition to the circuitry of the alarm portion 183 described in the preceding paragraph, the alarm portion 183 of the control circuit also includes circuitry which will sound the horn 184 and light the light-emitting diode 186 when the switch 137 and solenoid 140 are activated by the overpressure safety system for the hose 30; circuitry that will sound the horn 184 and light the light-emitting diode 188 when the switch 116 is activated due to low gas pressure in the gas supply network 10; circuitry that will sound the horn 184 and light the light-emitting diode 189 when the switch 89 is activated due to an inspiration phase of over 3.5 seconds in duration; and circuitry that will light a light-emitting diode 190 as a pilot light when the main power to the ventilator is switched on. The alarm portion 183 also includes circuitry which will light a light-emitting diode 187 upon electrical power failure to the ventilator when it is turned on. The circuitry includes a battery 200 and a switch 201 which is operated in conjunction with a main on-off switch for the ventilator (not shown). Switching on the ventilator via the main switch closes the switch 201 to couple the battery 200 to circuitry that will apply the battery voltage to the light-emitting diode 187 if the main power fails. A push button test switch 202 is also provided to give the operator means for testing the electricall strength of the battery 200.

A suitable power supply (not shown) is also included in the control circuit to provide the indicated voltages at the various power input terminals.

Normally, the pneumatic and electrical components of FIGS. 1, 2A and 2B will be mounted in a cabinet (not shown) except for the hose 30 and tube 126 which extend from the cabinet to an infant being ventilated; and the cabinet has a control panel on which the various light-emitting diodes, switches, control valves and other manually operated control devices described above are located.

The drawing filed with this application is informal and has the various component valves and nomenclature shown on the drawing. It is anticipated that when formal drawings are filed, the various components will be identified by reference numerals and the valves and nomenclature of the components will be shown in a table substituted for this paragraph.

It will be appreciated by those skilled in the art that many changes in the electronic and pneumatic circuitry could be made without departing from the spirit of the present invention. Thus the present invention should not be limited by the structure of the ventilator described above, but only by the structure described in the dependent claims and its equivalents.

I claim:

1. An infant ventilator including a gas delivery system comprising:
    an inlet end adapted to be coupled to a continuous source of gas under pressure;
    an outlet end;
    a mouthpiece between said ends adapted to be coupled to the breathing passageways of an infant;
    said system normally being continuously open to allow the flow of gas between said inlet and said outlet end, and further comprising:
    outlet valve means movable between a closed position blocking said outlet end for normally causing gas to be contained within said system and a generally uniform gas pressure at the mouthpiece to cause involuntary inspiration of an infant to which the mouthpiece is coupled, and an open position so that gas will flow from said inlet end past the mouthpiece and through said outlet end to the atmosphere while affording exhalation of the infant;
    means for switching said outlet valve means between said closed and opened positions in a predetermined time sequence;
    means for sensing pressures above a predetermined maximum in said delivery system between said inlet end and said mouthpiece including a portion movable from a first position to a second positon in response to said pressure above a predetermined maximum and being manually resettable from said second position to said first position; and
    means between said inlet end and said mouthpiece activated in response to movement of said portion to said second position for stopping flow of gas through said delivery system, and for exhausting a portion of said gas delivery system including said mouthpiece to the atmosphere until said portion is manually reset to said first position.

2. An infant ventilator according to claim 1, wherein said means for sensing comprises
    a housing;
    a permanent magnet fixed within said housing;
    a shaft assembly mounted within said housing and extending on both sides of said magnet, said shaft assembly being mounted for axial sliding movement between said first and second positions and comprising:
        a shaft;
        inner and outer magnetically attractable members fixed to said shaft on opposite sides of said magnet, said outer member being closely adjacent said magnet and said inner member being spaced from said magnet when said shaft assembly is in said first position; and said inner member being closely adjacent said magnet and said outer member being spaced from said magnet when said shaft assembly is in said second position; and
    a diaphragm coupled to said shaft adjacent said inner member;
    said housing and diaphragm defining a chamber coupled to said gas delivery sysem so that when said shaft assembly is in said first position pressure above said predetermined maximum will overcome the magnetic attraction between sid magnet and said outer member and cause said shaft assembly to suddenly shift to said second position under the influence of said pressure and the magnetic attraction between said inner member and said magnet;
    said means for stopping flow and for exhausting comprises valve means in said gas delivery system including said mouthpiece, said valve means having portions movable between a normal position for allowing flow of gas through said gas delivery system; and a second position for blocking flow of gas through the portion of said gas delivery system between said valve means and said inlet end, and for exhausting said portion of said gas delivery system including said mouthpiece; and
    means coupled between said means for sensing and said means for stopping flow and for exhausting for moving said valve means from said normal to said second postion upon movement of said shaft assembly from said first to said second position.

3. An infant ventilator according to claim 2, wherein said outer member is adjustable mounted for movement axially of said shaft to afford changing said predetermined maximum pressure.

4. An infant ventilator according to claim 1 or 2 further including means activated in response to gas pressure above said predetermined pressure being sensed by said means for sensing for activating an audible alarm.

5. An infant ventilator according to claim 1 or 2 further including means activated in response to gas pressure above said predetermined pressure being sensed by said means for sensing for activating a visible alarm.

* * * * *

UNITED STATES PATENT AND TRADEMARK OFFICE
CERTIFICATE OF CORRECTION

PATENT NO. : 4,466,433
DATED : August 21, 1984
INVENTOR(S) : David L. Robbins

It is certified that error appears in the above-identified patent and that said Letters Patent is hereby corrected as shown below:

Col. 1, line 57, "deliver" should read --delivery--.
Col. 9, line 26, "electricall" should read --electrical--.
Col. 10, line 44, "sysem" should read --system--.
Col. 10, line 47, "sid" should read --said--.
Col. 10, line 53 after "system" insert --between said inlet end and said portion of said gas delivery system--.
Col. 10, line 65, "postion" should read --position--.
Col. 10, line 68, "adjustable" should read --adjustably--.

Signed and Sealed this

Fifth Day of March 1985

[SEAL]

Attest:

DONALD J. QUIGG

Attesting Officer

Acting Commissioner of Patents and Trademarks